United States Patent [19]

Eichel et al.

[11] Patent Number: 5,026,559

[45] Date of Patent: Jun. 25, 1991

[54] SUSTAINED-RELEASE PHARMACEUTICAL PREPARATION

[75] Inventors: Herman J. Eichel; Brent D. Massmann, both of Columbus, Ohio

[73] Assignee: Kinaform Technology, Inc., Dayton, Ohio

[21] Appl. No.: 332,154

[22] Filed: Apr. 3, 1989

[51] Int. Cl.$^5$ ................................................ A61K 9/54
[52] U.S. Cl. ................................... 424/458; 424/474; 424/475; 424/480; 424/490
[58] Field of Search ............... 424/458, 474, 475, 480, 424/490

[56] References Cited

U.S. PATENT DOCUMENTS

| | | | |
|---|---|---|---|
| 3,115,441 | 12/1963 | Hermelin | 424/469 |
| 3,155,590 | 11/1964 | Miller et al. | 424/495 |
| 3,341,416 | 9/1967 | Anderson et al. | 424/495 |
| 3,488,418 | 1/1970 | Holliday et al. | 424/459 |
| 3,492,397 | 1/1970 | Peters et al. | 424/495 |
| 3,531,418 | 9/1970 | Fanger et al. | 427/213.3 |
| 4,025,613 | 5/1977 | Guy et al. | 424/472 |
| 4,520,009 | 5/1985 | Dunn | 424/78 |
| 4,572,833 | 2/1986 | Pederson et al. | 424/470 |
| 4,728,512 | 3/1988 | Mehta et al. | 424/458 |
| 4,752,470 | 6/1988 | Mehta | 424/458 |
| 4,808,413 | 2/1989 | Joshi et al. | 424/469 |

FOREIGN PATENT DOCUMENTS

| | | |
|---|---|---|
| 77956 | 3/1978 | European Pat. Off. |
| 11687 | 8/1979 | Japan. |
| 108269 | 3/1981 | Japan. |

OTHER PUBLICATIONS

Lehmann et al., Practical Course in Lacquer Coating, Rohm Pharma.

*Primary Examiner*—Thurman Page
*Assistant Examiner*—Leon R. Horne
*Attorney, Agent, or Firm*—Killworth, Gottman, Hagan & Schaeff

[57] ABSTRACT

A sustained-release pharmaceutical preparation comprising an admixture of uncoated and/or single walled coated drug, and multi-units of microparticles of a multi-walled coated drug. The microparticle structure preferably has a core drug, an inner wall microencapsular enteric coating, such as a polymethyacrylic acid/acrylic acid copolymer or cellulose acetate phthalate, a solid acid such as citric acid, adipic acid, or an acidic ion exchange resin layered onto or included in the enteric layer, and an outer wall microencapsulated control coating, such as a polymethacrylic acid ester copolymer or ethyl cellulose. The multi-walled coated drug has a delayed, gradual, long-term release which takes place in the intestines while the uncoated and/or single walled coated drug has immediate therapeutic properties upon dissolution in the stomach. The enteric coating and control coating may be applied to core drug granules by a coacervation, spray coating or other process. The acid may be a separate layer applied by a spray coating or other process.

18 Claims, No Drawings

SUSTAINED-RELEASE PHARMACEUTICAL PREPARATION

BACKGROUND OF THE INVENTION

The present invention relates to multi-unit sustained-release pharmaceutical preparations and the method for making them. More particularly, it relates to microparticles formed of granular drug soluble in digestive fluids, which drug is coated with a multi-wall structure to give a delayed and sustained drug delivery. The microparticles of multi-walled coated drug may be mixed or concentrically coated with immediate release drug and/or single walled coated drug to provide an improved sustained-release system.

As is well known, the maximum time of effectiveness in many pharmaceutical preparations, particularly those containing a drug such as aspirin, acetaminophen, indomethacin, propranolol hydrochloride, dextromethorphan, etc. is only a few hours because of biological modification and/or elimination of the medication in the body. Consequently, repeated dosages must be taken at frequent intervals to obtain long term therapeutic levels of drug. Furthermore, these drugs usually dissolve readily in the digestive juices and the total dosage is immediately fed into the blood stream. After high initial peak concentrations, the level of drug in the blood stream constantly decreases because of the biological elimination, so there is little or no therapeutic effect at the end of the period between dosages. As a result, the therapeutic effect fluctuates between dosages corresponding to the peaks and valleys in the level of drug in the blood as commonly measured by trough to peak ratios.

Many attempts have been made to develop timed-released pharmaceutical preparations which provide a more constant level of the drug in the blood over several hours.

One common approach is to microencapsulate aspirin, for example, with a capsule wall material which provides a slower dissolution rate than free aspirin. The early work in that regard is represented by U.S. Pat. Nos. 3,155,590; 3,341,416; 3,488,418; and 3,531,418. Those patents, among others, disclose dispersing particles of aspirin in a hot cyclohexane solution containing ethyl cellulose and then introducing a phase-separation inducing agent, such as butyl rubber or polyethylene. Upon cooling, the aspirin particles become coated with ethyl cellulose. The coated particles are then admixed with tableting excipients and formed into dosage-sized tablets. When ingested, the tablets disintegrate rapidly and the individual particles of encapsulated aspirin are dispersed in the stomach. The gastric juices slowly diffuse through the capsule walls, dissolve the aspirin, and the dissolved aspirin slowly diffuses or leaches out through the capsule walls into the body. Although the resultant blood level content is sustained to a measurable extent, the aspirin is diffused into the body rapidly enough so there is an initially high blood level content which decreases quite rapidly within a few hours. These dissolution properties yield undesirable blood aspirin concentration versus time curves.

In the first place, the time required to reach therapeutic levels after ingestion is longer for timed-release aspirin than for free aspirin. For this reason, it has been proposed that free aspirin be tableted with coated aspirin particles. See, for example, U.S. Pat. No. 3,115,441 which discloses mixing aspirin particles having a series of coatings thereon with uncoated aspirin, and tableting so that the coated particles are entrapped in uncoated aspirin. Tablets made according to the method have the advantage of providing immediate relief because the free aspirin (which comprises the initial dosage) dissolves immediately upon ingestion. However, as with the other preparations discussed above, the tablet rapidly disintegrates in the stomach.

See also Guy U.S. Pat. No. 4,025,613 where a multi-layered tablet is disclosed. One layer comprises aspirin coated with cellulose acetate phthalate and the other layer is free aspirin. However, as stated in Dunn, U.S. Pat. No. 4,520,009, while aspirin tablets prepared by the process of Guy exhibit desirable in vitro release properties, processing difficulties are encountered in production runs. Dunn, then, is said to be an improvement in that large batch processing is allegedly made easier. In Dunn an admixture of aspirin, microcrystalline cellulose, cellulose acetate phthalate, plasticizer, corn starch and lubricant is compressed into tablet form. There is no microencapsulation as such in Dunn and, accordingly, the advantages of multi-units dosage of microencapsulated particles are foregone in favor of processing ease.

With microencapsulated particles, as discussed above, the dissolution rate decreases rapidly and the blood aspirin concentration at 2-3 hours must greatly exceed the therapeutic level in order to maintain adequate aspirin concentrations at 8 hours. As a result, efforts have been made to adjust the rate of dissolution and, thus, control the timing of sustained drug release. See, for example, Peters U.S. Pat. No. 3,492,397 where the dissolution rate is said to be controlled by adjusting the wax/ethyl cellulose ratio of the applied spray coating, and Metha, U.S. Pat. No. 4,752,470 where the controlled release characteristics for indomethacin are varied depending on the ratio of ethyl cellulose to hydroxypropyl cellulose in the coating. See also U.S. Pat. Nos. 4,205,060 and 3,488,418 where it is indicated that the rate of dissolution of various drugs can be controlled by varying the thickness of the coating applied to those drugs.

Thus, not only aspirin, but other drugs soluble in digestive fluids have been treated or compounded in an effort to achieve a more controlled release of the drug in the digestive system. As mentioned, many of those attempts have involved encapsulation processes.

Another method for providing an encapsulated pharmaceutical composition is discussed in published European Patent Application No. 77,956, published May 4. 1983. EPO Publication No. 77,956 discloses the use of microcapsules containing a coated core material such as pharmaceutical compounds and foodstuffs. The coating is applied by dispersing the core material into a solution containing ethyl cellulose as the wall-forming material. A phase separation of the ethyl cellulose from the dispersion of core material is carried out by cooling the dispersion. During this cooling, an enteric polymer material is incorporated into the ethyl cellulose coating walls by adding the enteric polymer material with stirring while the ethyl cellulose is still in the "gel" state. The enteric polymer material thus added penetrates and is dispersed into the coating walls. When the microcapsules are administered, the release of the active compound does not generally occur in the stomach. However, the enteric polymer material is easily dissolved in the intestinal tract, thereby making the microcapsules porous. The porosity of the microcapsules promotes the rapid release of the active compound in the intestinal tract.

A similar approach is found in Japanese Patent publication No. 12614/81. published Mar. 23, 1981. Japanese Publication No. 12614/81 discloses an enteric protective coating composition which will not readily dissolve in acidic gastic juices, but rapidly (within minutes) dissolves at the pH found in the intestines. The enteric coating is an aqueous dispersion of, for example. hydroxy propyl methyl cellulose phthalate, a gelling agent such as diacetin, and hydroxy propyl methyl cellulose. See, also, Japanese Patent Publication No. 11687/81. published Mar. 16, 1981. which uses hydroxy propyl methyl cellulose phthalate as an enteric coating.

The systems described in the EPO and Japanese publications are essentially "delayed" release mechanisms. There is a delay of medicament release in the stomach, but once the coated medicament reaches the intestines, the release of medication is rapid. There is no sustained release of medication in the intestines.

Still other systems for encapsulating or coating pharmaceutical preparations are known. For example, Lehmann et al, Practical Course in Lacquer Coating (Rohm Pharma) discuss possible combinations of coating agents. Lehmann et al suggests using a multi-layered dragee design to achieve the desired release profile. Lehmann et al disclose using mixtures of EUDRAGIT acrylic resin retard coatings and lacquer substances that are resistant to gastric juices when the aim is to modify the release pattern. However, Lehmann et al do not disclose or suggest any specific formulations or guidelines for acheving a desired release profile.

Note should be made of Mehta et al, U.S. Pat. No. 4,728,512 which discloses using three distinct release formulations. The preparation consists of three groups of spheroids containing active medicinal substance. The first group of spheroids is uncoated and rapidly disintegrates upon ingestion to release an initial dose of medicinal substance, then a second group of spheroids is coated with a pH sensitive coat to provide a second dose, and finally a third group of spheroids is coated with a pH independent coat to provide a third dose. Metha et al use three distinct spheroids encapsulated in a capsule dosage rather than a single microencapsulated spheroid formulation. Consequently, the result is three distinct releases at different times rather than a uniform sustained release. Furthermore, there is very limited flexibility in achieving various release profiles when using this formulation.

Finally, reference is made to applicants' copending application Ser. No. 017.988, filed Feb. 24, 1987, the disclosure of which is hereby incorporated by reference. In the copending application there is disclosed a sustained-release pharmaceutical preparation comprising a dual walled coated drug having an inner wall microencapsular control coating, such as ethyl cellulose, and an outer wall enteric coating, such as cellulose acetate phthalate. Such a dual-walled material will release less than 10% per hour of core drug while in the stomach but will slowly release the core drug in the intestines to provide adequate drug levels for 8 or more hours. While this represents an improved result, a system which provides a longer delay in dissolution of drug from the slow release component would provide greater flexibility in designing sustained release profiles, especially for once-a-day sustained release formulations for a wide variety of drugs.

Accordingly, the need exists for a further improved sustained-release pharmaceutical preparation which has an extended dosing interval, provides more constant blood concentration levels, is economically produced, and has the advantages of a multi-units formulation.

SUMMARY OF THE INVENTION

The present invention meets that need by providing multi-units of microparticles in the form of a multi-walled coated medicament having a core drug, an inner wall enteric coating, preferably including a solid acid incorporated into or layered onto the enteric coating, and then an outer wall microencapsular control coating. After ingestion of the dosage, the acid within the enteric coating or the acid layer between the enteric core and the control coating impedes drug release by maintaining the enteric material at a low pH. Eventually, the acid is dissolved by the digestive fluids and diffuses out, or is neutralized. Subsequent to the removal or neutralization of the acid, the higher pH intestinal fluid diffuses into the enteric core and the drug is dissolved and released through the outer wall control coating in a controlled manner.

The length of time for the delay is controlled by the amount of the acid present and the rate of neutralization or solubility and diffusion of the acid, and/or the time required to dissolve or disperse the enteric material. The drug release rate subsequent to the delay is determined by the rate of drug dissolution from the core and the rate of diffusion through the outer wall control coating. Excess drug concentrations are minimized and steady long-term release of the drug is maximized.

The inner wall enteric coating is preferably a microencapsular one such as polymethacrylic acid/acrylic acid copolymer or cellulose acetate phthalate. Both are known coating materials. Inner wall enteric coatings of this nature greatly impede the release of the core drug at pH under 5 as provided by the acid, if included, or by the gastric fluid of the stomach. However, such enteric coatings dissolve at pH 5.5-7.5 as found after diffusion or neutralization of the acid, if present, to allow the release of the drug in the intestine. Other enteric coatings may be used as long as they do not readily dissolve or disperse in the acid environment provided by the acid incorporated into or layered onto the enteric layer, or by the gastric juices of the stomach but do dissolve or disperse in the intestinal fluid of the intestines. For example. hydroxypropyl methyl cellulose phthalate, polyvinyl acetate phthalate, hydroxyethyl ethyl cellulose phthalate, cellulose acetate tetrahydrophthalate, acrylic resin, cellulose acetate trimellilate or other film-forming materials which dissolve or disperse in the intestine but remain intact in the stomach are possible alternatives.

The acid is selected from the group consisting of any solid. non-toxic acid which can maintain the pH low enough to preserve the enteric properties of the core. For example, possible alternatives include citric acid, ascorbic acid, adipic acid, ethylene diamine tetracetic acid, lactic acid and succinic acid, or polymeric acids and acidic ion exchange resins, such as carboxymethylcellulose and Amberlite IRP-64 (Rohm and Haas, Philadelphia, Penn.).

The outer wall microencapsular control coating is preferably selected from the group consisting of methacrylic acid ester copolymers and ethyl cellulose. Both are common microencapsular coatings which will not readily dissolve or disperse in the stomach or intestines, but which permit release of the water-soluble drug through the capsule wall.

The core drug should be one which is reasonably soluble in the digestive fluids as to be slowly releasable in the intestines through the outer wall microencapsular control coating. Preferred are aspirin, acetaminophen, indomethacin, propranolol hydrochloride, dextromethorphan hydrobromide, disopyramide phosphate and furosemide. Other usable drugs soluble in the digestive fluids include various vitamins, minerals, antibiotics, and other analgesics. The preferable size range of drug ganules is from about 100 to about 2000 microns, more preferably around 500 to 800 microns.

The drug granules are preferably microencapsulated with an enteric coating by a coacervation, spray coating or other process. The outer wall control coating is also preferably applied by a coacervation, spray coating or other process. The spray coating process is most preferred. The coating level of the microencapsulated core drug with the enteric coating is preferably from approximately 4 to 25% of the total weight of the enteric coated bead depending on the granule size and drug solubility. This results in an inner wall thickness of between about 5 and about 100 microns. When the acid is present as a separate layer it is also applied by spray coating or other processes. The coating level for the acid layer is preferably 0 to 50% of the total weight of the acid coated bead, depending on the time delay desired. This results in an acid layer thickness of between 0 and about 150 microns. Alternatively, acid may be included in the enteric coat ranging from approximately 0 to 50% of the total weight of the coat. The coating level of the acid and enteric combination is preferably 4 to 50% resulting in an inner wall thickness of approximately 5 to 200 microns. The coating level of outer wall microencapsular control coating is preferably from approximately 3% to 20% of the total weight of the finished bead, and more preferably from approximately 4% to 10%, depending on granule size, drug solubility, and desired release rate. This results in an outer wall thickness of about 5 to about 50 microns. The total microparticle size is around 110 to 2300 microns. Multiunits of these microparticles are combined in a gelatin capsule or pressed into a tablet to achieve the desired dosage level.

In this form, the multi-walled coated medicament will not release significant amounts of drug in the stomach. However, the inner wall enteric coating will dissolve or disperse in the intestines after the acid if initially present within the microcapsule is neutralized or dissolves and diffuses away. Because the outer wall microencapsulated control coating remains, the drug is slowly and steadily released in the intestines.

The multi-unit microparticles may also be admixed or concentrically coated with other fractions of free and/or time-release drug. The admixture may be placed in either capsules or tablets along with other usual ingredients such as binders, fillers, lubricants, etc. In this form free drug is released immediately in the stomach. The multi-walled coated medicament does not release drug in the stomach; but rather, in the intestines. After a time delay determined by the amount of acid included in the microcapsule, drug is released slowly and steadily from the multi-walled coated portion of the admixture by reason of the mechanism discussed above. The admixture, thus, provides for both immediate and delayed sustained release of the drug.

Whether the microparticles of the present invention are packaged with free or single wall coated drug or not, the follow benefits are obtained by use of multiunits of these microparticles:

(a) There is a more uniform and longer sustained release of the drug because each microparticle acts individually and is dispersed throughout the gastrointestinal tract to give a statistically beneficial release, (b) Potential irritation of the gastrointestinal tract by the drug is minimized because of the small, localized, individual release by each microparticle, and (c) The danger of overdosing, due to the "burst", "surge" or "dump" effect known to occur with large non-sustained-release dosages or premature release of sustained-release dosages due to defects, is virtually eliminated because the small, individually-releasing microparticles ensure sustained statistical release. A premature release by a defective microparticle is insignificant since each microparticle is only a fraction of the total drug dosage.

Accordingly, it is an object of the present invention to provide a sustained-release pharmaceutical preparation which has desirable release kinetics and yet has a better therapeutic index and/or is more economical to produce and posseses the desirable characteristics of a multi-unit dosage. It is another object of the present invention to provide a multi-walled coated medicament which may be used either alone or may be combined with other fractions of free and/or timed-release drug as a sustained-release pharmaceutical preparation.

Other objects and advantages of the present invention will be apparent from the following description and the appended claims.

DESCRIPTION OF THE PREFERRED EMBODIMENTS

The preferred multi-walled coated medicament of the present invention is a granular core drug microencapsulated with a polymethacrylic acid/acrylic acid copolymer or cellulose acetate phthalate inner enteric coating, followed by a citric acid, adipic acid, or an acidic ion exchange resin layer, and, then, an ethyl cellulose or a methacrylic acid ester copolymer outer wall microencapsulated control coating. An alternative preferred embodiment is the inclusion of citric acid in polymethacrylic acid/acrylic acid enteric coat instead of layering the acid onto the enteric coat.

Examples of drugs which may be used as the core drug include most preferably aspirin, acetaminophen, indomethacin, propranolol hydrochloride, furosemide, disopyramide phosphate, and dextromethorphan hydrobromide. In addition to these classes of drugs, others may also be used. For example, vitamins, minerals, antibiotics, and analgesics may be used as the core drug. As long as the drug has sufficient solubility to be releasable in the intestines through the outer wall microencapsular control coating, is or can be made granular, i.e. from about 100 to about 2000 microns in size, and is capable of having the multi-wall structure of the present invention applied to the granular drug, it is usable.

As mentioned, the outer wall microencapsular control coating should be one which does not readily dissolve or disperse in either the stomach or the intestines. It must, however, permit the aqueous intestinal fluids to diffuse through the capsule wall, dissolve the water-soluble core drug, and slowly diffuse or leach out through the capsule wall. It should also be a material which is preferably applicable by coacervation, spray coating or other processes to the granular drug.

Cellulose acetate phthalate or a polymethacrylic acid/acrylic acid copolymer is the preferred inner wall enteric coating. These materials are also particularly preferred because they form an impermeable barrier which will not readily dissolve or disperse at the low pH provided by the acid included in the microcapsule or by the gastric juices in the stomach. Rather, they remain undissolved under those conditions. And yet, at the higher pH of the intestinal fluids these enteric coatings will dissolve or disperse. Other materials which may be used for such purposes are hydroxypropyl methyl cellulose phthalate, polyvinyl acetate phthalate, hydroxyethyl ethyl cellulose phthalate, cellulose acetate tetrahydrophtalate, acrylic resin, cellulose acetate trimellitate and phthalate or polyphthalate esters of film-forming polymers such as those already mentioned.

In a fluid bed spray coating process, an inner wall enteric coating is formed by spraying cellulose acetate phthalate or a polymethacrylic acid/acrylic acid copolymer onto a granular core drug such as dextromethorphan. Subsequently, the inner wall enteric coating is allowed to dry. An acid layer, such as citric acid, adipic acid or an acidic ion exchange resin is then spray coated onto the inner wall enteric coating. After allowing the acid layer to dry, an outer wall microencapsulated control coating is spray coated onto the acid layer.

The coating level of the inner wall enteric coating phase is preferably from approximately 4% to 25% and more preferably from approximately 5% to 10%. The coating level of acid layer is preferably 0 to 50%. The coating level of the outer wall microencapsular coating is preferably from approximately 3% to 20% and more preferably from approximately 4% to 10%. The coating levels determine the wall thickness, as discussed above, resulting in an inner wall thickness range of about 5 to about 100 microns, an acid layer thickness of about 0 to 150 microns and an outer wall thickness of about 5 to 50 microns. Alternatively, the acid layer and enteric layer may be combined into a single layer, preferably containing 0 to 50% acid by weight. The coating level for this layer is preferably 4 to 50%, resulting in a wall thickness of 5 to 200 microns. The outer wall control coat is then applied as described above.

The length of time for the delay is controlled by the amount of acid present in the microcapsule and the rate of solubility and diffusion or neutralization of the acid. As mentioned, the drug release rate after the delay is determined by the rate of drug dissolution from the core and the rate of diffusion through the barrier. Tables below illustrate that the acid maintains the impermeability of the enteric layer which impedes drug release for as long as 4 hours.

EXAMPLE I

Two sustained-release pharmaceutical preparations having 28% active dextromethorphan, a 16% enteric coat, a 20% citric acid coat, and 4% and 6% control coats were prepared using the Wurster process as follows:

A. Dextromethorphan beads (28%) were prepared by Wurster coating 25/30 mesh sugar spheres with the following Formula 1:

| Formula 1 Dextromethorphan Hydrobromide Layering Formula | |
| --- | --- |
| Dextromethorphan HBr | 40% |
| Opadry (1) YS-1-7006 | 5% |
| Talc | 2% |
| Water | 53% |

(1) A binder, from Colorcon, of West Point, PA.

B. The dextromethorphan beads were, then, Wurster coated to produce a 16% coat of inner enteric coating with the following Formula 2:

| Formula 2 Enteric Coating Formula | |
| --- | --- |
| Eudragit L30D (3) | 70% |
| Myvacet 9-40 (4) | 3% |
| Talc | 2% |
| Tween 80 (5) | 0.2% |
| Water | 24.8% |

(3) A polymethacrylic acid/acrylic acid copolymer from Rohm Pharma GMBH, of Weiterstadt, W. Germany.
(4) A plasticizer, from Distallation Products, Inc. of Rochester, NY.
(5) An emulsifying agent, from ICI Americas, of Newcastle, DE.

C. The inner enteric coated dextromethorphan beads were, then, Wurster coated with 20% citric acid using the following Formula 3:

| Formula 3 Citric Acid Layering Formula | |
| --- | --- |
| Citric Acid | 45% |
| Povidone K30 (6) | 6% |
| Talc | 4% |
| Water | 45% |

(6) A binder, from GAF, of Texas City, TX.

D. Finally, 4% and 6% outer control coats were applied by the Wurster process using the following Formula 4:

| Formula 4 Control Coat Formula | |
| --- | --- |
| Eudragit E30D (7) | 71.5% |
| Magnesium Stearate | 3.5% |
| Water | 25.0% |

(7) A methacrylic/acrylic acid ester copolymer, from Rohm Pharma GMBh, of Weiterstadt, W. Germany.

The resulting microparticles had an average granular core drug diameter (i.e. dextromethorphan bead) of approximately 750 microns, an inner enteric coating approximately 20 microns thick, a solid acid layer approximately 30 microns thick, and outer control coats approximately 5 and 8 microns thick for a total average microparticle diameter of approximately 850 microns.

E. A dissolution study was conducted with the above prepared microcapsules as follows:

TABLE I

| | % Dissolved | |
| --- | --- | --- |
| Elapsed Time | 4% Control Coat | 6% Control Coat |
| 0.50 hrs. | 0 | 0 |
| 1.00 hrs. | 1.3 | 0 |
| 1.50 hrs. | 6.7 | 2.5 |
| 2.00 hrs. | 9.4 | 2.7 |
| 3.00 hrs. | 20.2 | 7.2 |
| 5.00 hrs. | 36.9 | 14.8 |

The tests were performed using the USP XXI basket method. The basket was loaded with approximately 500 mg of sample and rotated at 50 RPM for 5 hours in a 1 liter vessel, containing a buffer with a pH of the intestinal fluids, i.e. pH 6.8. As Table I exhibits, the 20% acid layer maintains the impermeability of the 16% enteric layer for about 2 hours and thereby provides the desired delayed and sustained-release of the drug (dextromethorphan in Table I). As can be seen, once the acid diffuses out or is neutralized and the enteric polymer is converted from the acid to the salt form, the core drug diffuses out of the microcapsule at a controlled rate. Using a thinner control coat reduces the delay time and increases the drug release rate.

EXAMPLE II

A second batch of microparticles were prepared. These microparticles were prepared as in Example I with a 6% control coat except that the dextromethorphan beads were 22.2% active drug and the following Formula 5 was used for the 20% acid layer:

| Formula 5 Adipic Acid Layering Formula | |
|---|---|
| Adipic Acid | 26.5% |
| Povidone K90 (6) | 3.5% |
| Water | 70.0% |

(6) As in Example I.

The resulting microparticles had an average granular core drug of approximately 725 microns, an inner enteric coating approximately 20 microns thick, a solid acid layer approximately 30 microns thick, and an outer control coat approximately 8 microns thick for a total average microparticle size of approximately 850 microns.

Again a dissolution study was conducted with the following results:

TABLE II

| Elapsed Time | % Dissolved |
|---|---|
| 0.50 hr. | 0 |
| 1.00 hr. | .5% |
| 1.50 hr. | 2.5% |
| 2.00 hrs. | 5.3% |
| 3.00 hrs. | 15.7% |
| 5.00 hrs. | 37.8% |

The same USP XX basket method used in the aforementioned tables. Table II illustrates that adipic acid will also maintain the inner wall enteric coat in the impermeable acid state. Therefore, the addition of an adipic acid layer, like the citric acid layer, will also provide the desired delayed and sustained-release of drug.

EXAMPLE III

A sustained-release pharmaceutical preparation having 24% dextromethorphan, a 16% enteric coat, no acid and varying amounts of control coat was prepared as follows:

A. Dextromethorphan beads were prepared as in Example I. except that the amount of Formula 1 was adjusted so that the active drug amount is 24%.

B. The 24% active dextromethorphan beads, approximately 725 microns in diameter, were, then, coated with an inner enteric coating as in Example IB forming an enteric coat approximately 20 microns thick.

C. Unlike Example I, no acid layer was used.

D. Two different runs were produced having 4% and 6% of a control coat using Formula 4 as in Example ID. Coat thicknesses were approximately 5 and 8 microns.

E. A dissolution study was conducted with the two runs of microcapsules as follows:

TABLE III

| Elapsed Time | 4% Control Coat Dissolved | 6% Control Coat Dissolved |
|---|---|---|
| 0.50 hr. | 8.9% | 0.4% |
| 1.00 hr. | 27.2% | 7.0% |
| 1.50 hrs. | 39.7% | 12.5% |
| 2.00 hrs. | 52.0% | 22.0% |
| 3.50 hrs. | 77.1% | 36.3% |
| 5.00 hrs. | 90.6% | 52.4% |

The results in Table III again illustrate that decreasing the control coat layer increases the rate at which the enteric coat becomes permeable and thereby releases the drug without the desired delay prior to the sustained-release. Furthermore, the results show the desirability of the preferred embodiment containing an acid layer as exemplified by the more rapid dissolution when an acid layer is not used. It is believed that acid layer impedes the drug release by maintaining the enteric coat in the impermeable acid form which results in the desired delay of drug release.

EXAMPLE IV

A sustained-release propranolol hydrochloride preparation having 35% active drug, a 30% enteric coat, no acid layer, and varying amounts of control coat was prepared as follows:

A. 25/30 mesh sugar spheres were layered with propranolol hydrochloride to form 35% active beads using the following formula:

| Formula 6 Propranolol Layering Formula | |
|---|---|
| Propranolol | 35.7% |
| Opadry (1) | 4.5% |
| Talc | 1.8% |
| Water | 58.0% |

(1) As in Example I

B. The approximately 775 micron diameter propranolol hydrochloride beads were, then, coated to produce a 30% coat of inner enteric coating using Formula 2 as in Example IB to produce an inner wall approximately 50 microns thick.

C. Unlike Example I, no acid layer was used.

D. Three different runs were produced having 6%, 9% and 12%, respectively, of a control coat using Formula 4 as in Example ID. The control coat thickness were approximately 10, 15, and 20 microns. The diameter of the resulting microcapsules was approximately 900 microns.

E. A dissolution study was conducted with the three runs of microcapsules as follows:

TABLE IV

| Elapsed Time | 6% Control Coat Dissolved | 9% Control Coat Dissolved | 12% Control Coat Dissolved |
|---|---|---|---|
| 1.00 hr. | 0% | 0% | 0% |
| 2.00 hrs. | 0.1% | 0% | 0% |
| 3.00 hrs. | 2.2% | 0.7% | 0.2% |
| 4.00 hrs. | 8.0% | 3.1% | 1.3% |
| 6.00 hrs. | 26.2% | 9.9% | 5.1% |
| 12.00 hrs. | 67.9% | 32.9% | 8.4% |
| 16.00 hrs. | 83.2% | 45.4% | 34.0% |
| 20.00 hrs. | 91.8% | 55.3% | 42.3% |
| 24.00 hrs. | 98.0% | 64.0% | 51.2% |

The dissolution study shown in Table IV utilized first a two hour sequence at pH 1.1 (simulating stomach fluids), followed by a pH 6.8 buffer (simulating intestinal fluids) for hours 3-24. As in Example III, the effect of increasing the control coat thickness is evident.

The dissolution procedure may also be performed using simulated digestive fluids. The composition of the buffers and digestive fluids is described in USP XX. In this instance simulated intestinal fluid is substituted for pH 6.8 buffer. Use of the digestive fluids is preferred if enzymes affect dissolution and is necessary if the coating contains lipid polymers or other enzymatically-degradable materials. However, neither of these conditions exists in the dissolution tests of the tables above (or The Tables below) and performing the dissolutions in simulated digestive fluids does not significantly affect the dissolution rates of the multi-walled coated medicament of the present invention.

EXAMPLE V

This example illustrates the formation of the multi-walled microcapsules of this invention by the preferred spray coating technique.

1200 g. of a granulated aspirin (Asagran 1640) was placed in the Wurster bowl of a Uniglatt fluid bed spray coating machine. The inner coating dispersion was prepared by adding 325 g. of water, slowly stirred, in a blender, 12 g. of talc (2755 Lo-micron Talc USP, from Whittaker), 0.75 g. antifoam agent (Medical Antifoam AF Emulsion, from Dow Corning) and 10 g. polyethylene glycol 8000 (from Baker). This suspension was poured into 400 g. of Eudragit L 30 D aqueous acrylic resin dispersion, a polymethacrylic acid/acrylic acid copolymer (from Rohm Pharma). Subsequent to application of this 10% enteric coating, the aspirin was dried and cooled.

The outer microencapsular wall was also applied by fluid bed spray coating. 1200 g. of the enteric coated aspirin (Asagran 1640, Monsanto) was placed in the Wurster bowl of a Uniglatt fluid bed spray coating machine. A dispersion of 120 g. Aqueous ethyl cellulose dispersion (FMC Corporation), 9 g. Myvacet 9-40 acetylated monoglycerides (Eastman Chemical Products) and 20 g. water was sprayed onto the aspirin to produce a 3.2% control coat. Subsequently, the microcapsules were allowed to dry and cool.

The core drug particles have a diameter ranging from 400 to 1100 microns. The inner wall enteric coat is approximately 15 microns thick. The outer wall control coat is approximately 5 microns thick.

The same basket dissolution method used in conjunction with the data set forth in the previous Tables was used to test the multi-walled microcapsules prepared in this example. The data from the tests of multi-walled microcapsules prepared by spray coating is set forth in Table V-A and Table V-B. Table V-A shows that the dual wall structure effectively precludes dissolution (and drug release) in the pH 1.1 buffer which simulates conditions in the stomach where the digestive fluids have approximately the same pH. Table V-B illustrates that the aspirin is released in a controlled manner in the pH 7.5 buffer which simulates conditions in the intestine.

TABLE V-A

| pH 1.1 HCl/NaCl Buffer | |
|---|---|
| ELAPSED TIME | % DISSOLVED |
| 1 hr. | <10 |

TABLE V-A-continued

| pH 1.1 HCl/NaCl Buffer | |
|---|---|
| ELAPSED TIME | % DISSOLVED |
| 2 hrs. | <10 |

TABLE V-B

| pH 7.5 Phosphate Buffer | |
|---|---|
| ELAPSED TIME | % DISSOLVED |
| 1 hr. | 32 |
| 2 hrs. | 47 |
| 4 hrs. | 63 |

EXAMPLE VI

In this example the acid is included in the enteric layer. A sustained release pharmaceutical formulation having 28% active indomethacin beads, a 27% inner wall enteric coat containing 35% citric acid, and 6% outer wall diffusion barrier control coat was prepared using the Wurster process. The percent coating level used in these examples is calculated by dividing the weight of the coat applied by the total weight of the beads after application of that coat.

A. Indomethacin beads (28% active drug) were prepared by Wurster coating 25/30 mesh sugar spheres with the following formula:

| Indomethacin | 30% |
|---|---|
| Opadry (1) | 5% |
| Water | 65% |

(1) As in Example I.

B. The Indomethacin beads were then coated to produce a 27% inner wall enteric coat containing 35% citric acid using the following formula:

| Eudragit L30D (3) | 52% |
|---|---|
| Citric acid | 10.5% |
| Myvacet 9-40 (4) | 2.3% |
| Talc | 1.6% |
| Tween 80 (5) | 0.1% |
| Water | 33.5% |

(3), (4) and (5) As in Example I.

C. The outer wall control coat of 6% was applied using the following formula:

| Eudragit NE30D (7) | 71.5% |
|---|---|
| Magnesium stearate | 3.5% |
| Water | 25% |

(7) As in Example I.

The above prepared microcapsules have a drug bead diameter of approximately 725 microns. The inner wall enteric and acid layer is approximately 40 microns thick and the outer wall control coat is approximately 10 microns. The diameter of the finished microcapsule is approximately 825 microns.

D. A dissolution study was conducted with the above prepared microcapsules using the USP XXI basket method. The basket was loaded with approximately 400 mg. of microcapsules and rotated at 50 rpm for 2 hours in 750 ml 0.1N HCl to model gastric pH. 250 ml of 0.2M Na$_3$PO$_4$ was added to adjust the pH to 6.8 to model intestinal conditions. The results are shown below.

TABLE VI

| Elapsed Time (hrs.) | % Dissolved |
| --- | --- |
| 1 | 0 |
| 2 | 0.5 |
| 3 | 2 |
| 4 | 3 |
| 6 | 17 |
| 8 | 27 |
| 12 | 46 |
| 16 | 64 |
| 20 | 75 |
| 24 | 85 |

As Table VI exhibits, the citric acid included in the enteric coat maintains the impermeability of the enteric layer for 4 hours. Thereafter, the dissolution occurs at a controlled rate. A combination of approximately 15% free drug with approximately 85% of these microcapsules in a single oral dose will provide an initial immediate dose of indomethacin followed 4 hours later by a second sustained release dose. Computer modeling of in vivo performance indicates that this formulation will maintain therapeutic drug levels for 24 hours while avoiding supra-therapeutic peak concentrations.

EXAMPLE VII

Microcapsules were prepared as in Example VI except samples were taken at control coat levels of 2% and 4%. Dissolutions were performed as in Example VI, except the pH was maintained at 6.8 throughout the dissolution. As can be seen in the table below increasing the coating thickness increases the delay time and decreases the dissolution rate after the delay.

TABLE VII

| Elapsed Time (hrs.) | 2% Coat % Dissolved | 4% Coat % Dissolved | 6% Coat % Dissolved |
| --- | --- | --- | --- |
| 1 | 42 | 4 | 1 |
| 2 | 62 | 14 | 2 |
| 4 | 79 | 36 | 10 |
| 6 | 87 | 51 | 21 |

EXAMPLE VIII

Microcapsules were prepared as in Example VI above except that the inner wall coating level was 10% instead of 27%. The thickness of the inner wall is approximately 15 microns. A dissolution was performed as in Example VI. As can be seen in the table below, by comparison with Example VI. decreasing the inner wall coat from 27% to 10% reduced the delay time from 4 hours to 2 hours.

TABLE VIII

| Elapsed Time (hrs.) | % Dissolved |
| --- | --- |
| 1 | 0 |
| 2 | 0 |
| 3 | 5 |
| 4 | 11 |
| 6 | 21 |

EXAMPLE IX

34% furosemide beads coated with a 5% enteric coat, a 20% acidic ion exchange resin (Amberlite IRP-64) layer, and 14% diffusion barrier control coat were prepared by the Wurster process.

A. 34% furosemide beads were prepared by layering 35/40 mesh sugar spheres with the following formulation:

| Furosemide | 25% |
| --- | --- |
| Povidone K30 (6) | 8% |
| Talc | 7% |
| Tween 80 (5) | 0.2% |
| Water | 59.8% |

(5) and (6) as in Example I.

B. A 5% enteric coat was applied using the following formulation:

| Eudragit L30D (3) | 70% |
| --- | --- |
| Myvacet 9-40 (4) | 3% |
| Talc | 2% |
| Tween 80 (5) | 0.2% |
| Water | 24.8% |

(3), (4) and (5) as in Example I

C. A 20% layer of Amerlite IRP-64 acidic ion exchange resin was applied to the enteric coated drug beads using the following formula:

| Amberlite IRP-64 (8) | 13% |
| --- | --- |
| Opadry YS-1-7006 (1) | 2% |
| Povidone K30 (6) | 6% |
| Water | 79% |

(1) and (6) as in Example I

D. A 14% diffusion barrier control coat was applied to the above beads using Formula C of Example VI. The resulting microcapsules had a drug bead diameter of approximately 600 microns, a 5 micron thick enteric coat, a 25 micron acid layer, and a 15 micron control coat. The overall diameter of the microcapsule was approximately 700 microns.

A dissolution was performed on the microcapsules using the procedure described in Example VI. The results are tabulated below:

TABLE IX

| Elapsed Time (hrs.) | % Dissolved |
| --- | --- |
| 1 | 0.5 |
| 2 | 1 |
| 3 | 3 |
| 4 | 7 |
| 6 | 18 |
| 8 | 33 |
| 12 | 70 |
| 16 | 87 |
| 20 | 96 |
| 24 | 99 |

As shown in the table, the acidic ion exchange resin maintains the impermeability of the enteric core for about 4 hours. Thereafter, the drug dissolves in a controlled manner. This illustrates that the acidic ion exchange resin layered onto the enteric coat maintains the enteric material in the impermeable form for the desired period of time.

Other layering geometries can also provide delayed and sustained release of drug. For example, another layer of water-soluble drug may be layered onto the outer wall control coating to provide immediate release of drug. This layering geometry consists of the core drug, followed by the enteric inner wall layer, the acid layer, the outer wall control coating and finally another drug layer to provide immediate drug release in the stomach. Another possible layering geometry may consist of this configuration and another control coat layer applied onto the outer drug layer which thereby provides a slower immediate release of drug in the stomach.

Another example of a layering geometry based upon the present invention would consist of the drug core followed by the enteric layer, an acid layer, then another drug layer and finally the outer wall control coating. This configuration also provides a slower release of drug in the stomach as opposed to the immediate release obtained without an outer control coat layer. Yet another example of a geometry which can provide a delayed and sustained-release of drug consists of a drug core coated with a control coat, an enteric layer, an acid layer and a second diffusion barrier. In all of these geometries, the essential element for providing delayed sustained release is an acid layer which impedes drug release from an enteric core until the acid diffuses out or is neutralized and/or the enteric core is dissolved by the higher pH intestinal fluid. The acid layer and the enteric layer may be combined into a single layer.

While the product and method herein described constitute preferred embodiment of the invention, it is to be understood that the invention is not limited to this precise product and method, and that changes may be made therein without departing from the scope of the invention.

We claim:

1. A sustained-release pharmaceutical preparation comprising an admixture of:
   (a) immediate release drug which will release in the stomach, and;
   (b) multi-units of microparticles, said microparticles comprising a core, an inner wall, a solid acid layer, and an outer wall, said core being a drug which is the same as said immediate release drug, said inner wall being a microencapsular enteric coating which will not dissolve or disperse readily in the stomach, but which dissolves or disperses in the intestines, said solid acid layer being incorporated in or layered onto said inner wall microencapsular enteric coating in order to preserve the impermeability of the enteric coating and delay drug release, and said outer wall being a microencapsular control coating which will not dissolve or disperse readily in the intestines, but which permits release of said drug through said microencapsular control coating.

2. The sustained-release pharmaceutical preparation of claim 1 wherein said inner wall enteric coating is selected from the group consisting of polymethacrylic acid/acrylic acid copolymer, cellulose acetate phthalate, hydroxypropyl methyl cellulose phthalate, polyvinyl acetate phthalate, hydroxyethyl ethyl cellulose phthalate, cellulose acetate tetrahydrophthalate, acrylic resin, and cellulose acetate trimellitate.

3. The sustained-release pharmaceutical preparation of claim 2 wherein said outer wall microencapsular control coating is selected from the group consisting of methacrylic acid ester copolymer and ethyl cellulose.

4. The sustained-release pharmaceutical preparation of claim 3 wherein said drug is selected from the group consisting of aspirin, acetaminophen, indomethacin, propranolol hydrochloride, dextromethorphan hydrobromide, disopyramide phosphate an furosemide.

5. The sustained-release pharmaceutical preparation of claim 1 wherein said acid is selected from the group consisting of citric acid, ascorbic acid, adipic acid, ethylene diamine tetracetic acid, lactic acid, succinic acid, polymeric acids, and acidic ion exchange resins.

6. The sustained-release pharmaceutical preparation of claim 1 wherein said drug is indomethacin, said inner wall microencapsular enteric coating is a polymethacrylic acid/acrylic acid copolymer and said outer wall microcapsular control coating is a methacrylic acid ester copolymer.

7. The sustained-release pharmaceutical preparation of claim 6 wherein said admixture consists of about 15% uncoated drug, and 85% multi-walled coated medicament.

8. A multi-walled coated medicament comprising:
   (a) a core containing a water-soluble drug,
   (b) an inner wall microencapsulated enteric coating selected from the group consisting of polymethacrylic acid/acrylic acid copolymer, cellulose acetate phythalate, hydroxethyl ethyl cellulose phythalate, cellulose acetate tetrahydroxphthalate acrylic resin, and cellulose acetate trimellitate,
   (c) an acid selected from the group consisting of citric acid, ascorbic acid, acidic acid, ethylene diamine tetracetic acid, lactic acid, succinic acid, polymeric acids and acidic ion exchange resins incorporated in or layered onto said inner wall microencapsular enteric coating in order to preserve the impermeability of the enteric polymer and delay drug release, and
   (d) an outer wall microencapsular control coating selected from the group consisting of methacrylic acid ester copolymer and ethyl cellulose being over said enteric coating and said acid.

9. The multi-walled coated medicament of claim 8 wherein said core drug is selected from the group consisting of aspirin, acetaminophen, indomethacin, propranolol hydrochloride, dextromethorphan hydrobromide, disopyramide phosphate and furosemide.

10. The multi-walled coated medicament of claim 9 wherein said inner wall enteric coating is a polymethacrylic acid/acrylic acid copolymer.

11. The multi-walled coated medicament of claim 10 wherein said acid layer coating is citric acid.

12. The multi-walled coated medicament of claim 11 wherein said outer wall microencapsular control coating is a methacrylic acid ester copolymer.

13. The multi-walled coated medicament of claim 12 wherein said core drug is indomethacin.

14. The multi-walled coated medicament of claim 13 wherein said water-soluble drug is 28%, said inner wall enteric coating is 27%, said acid is layered onto said inner wall enteric coating and is 35% and said outer wall microencapsular control coating is 6% by weight.

15. The multi-walled coated medicament of claim 8 wherein a second said water-soluble drug layer is outside said outer wall microencapsular control coating.

16. The multi-walled coated medicament of claim 15 wherein a second said outer wall microencapsulated control coating is outside said second water-soluble drug layer.

17. The multi-walled coated medicament of claim 8 wherein a second said water-soluble drug layer is between an acid layer and said outer wall microencapsulated control coating.

18. The multi-walled coated medicament of claim 8 wherein a second said outer wall microencapsulated control coating is between said water-soluble drug and said inner wall microencapsulated enteric coating.

* * * * *

UNITED STATES PATENT AND TRADEMARK OFFICE
CERTIFICATE OF CORRECTION

PATENT NO. : 5,026,559
DATED : June 25, 1991
INVENTOR(S) : Herman J. Eichel et al It is certified that error appears in the above-indentified patent and that said Letters Patent is hereby corrected as shown below:

Column 16, lines 19 and 20, "phythalate, hydroxethyl ethyl cellulose phythalate, cellulose acetate tetrahydroxphthalate" should be --phthalate, hydroxethyl ethyl cellulose phthalate, cellulose acetate tetrahydroxyphthalate--.

Signed and Sealed this

Twenty-third Day of November, 1993

Attest:

BRUCE LEHMAN

Attesting Officer        Commissioner of Patents and Trademarks